United States Patent [19]

Sobolewski

[11] 4,057,219
[45] Nov. 8, 1977

[54] COUNTERPOISING LOAD SUPPORT APPARATUS AND METHOD

[75] Inventor: Valentine S. Sobolewski, Muskego, Wis.

[73] Assignee: General Electric Company, Schenectady, N.Y.

[21] Appl. No.: 721,363

[22] Filed: Sept. 8, 1976

Related U.S. Application Data

[62] Division of Ser. No. 574,581, May 5, 1975, Pat. No. 4,003,552.

[51] Int. Cl.² .................................................. B66D 1/48
[52] U.S. Cl. ...................................... 254/175; 254/167; 187/71
[58] Field of Search .................. 254/174, 175, 173 R, 254/167, 183, 184, 168, 150 R; 197/71; 212/39 R; 242/128; 188/174, 196 R, 196 B, 196 BA

[56] References Cited
U.S. PATENT DOCUMENTS

| 1,942,144 | 1/1934 | Fuller ................................. | 254/175 |
| 2,254,910 | 9/1941 | Richards et al. ................... | 254/175 |

FOREIGN PATENT DOCUMENTS

521,515  10/1939  United Kingdom .................. 187/71

Primary Examiner—Robert J. Spar
Assistant Examiner—Kenneth Noland
Attorney, Agent, or Firm—Ralph G. Hohenfeldt

[57] ABSTRACT

In a device for counterpoising a range of cable supported loads, the inner end of a torsion spring is fastened to a shaft. A cam having an axially extending spiral cable groove of continuously varying radius is journaled on the shaft and the outer end of the spring is fastened to the cam. Means are provided to preload the spring to the onset of the useful portion of its torque versus revolution; relationship. A load supporting cable is wound on the cam with one end fastened at the largest radius end of the cam and with the load supporting portion of the cable having a first point of tangency with a smaller radius point in the groove when the load is in its uppermost position. Any load subject to a predetermined vertical travel distance will be counterpoised at all elevations by selecting a predetermined point of tangency in which case only one cam is needed for a range of load weights. The cam serves as a composite of individual cams for different loads. A new safety device and a new means for reducing nonconcentric winding of the counterpoise torsion spring are also provided.

3 Claims, 16 Drawing Figures

COUNTERPOISING LOAD SUPPORT APPARATUS AND METHOD

This is a division of application Ser. No. 574,581, filed May 5, 1975, now U.S. Pat. No. 4,003,552.

BACKGROUND OF THE INVENTION

This invention relates to apparatus for supporting a range of different loads or weights such that if the load is positioned manually at any elevation it will be counterpoised at that elevation.

The new load supporting apparatus will be exemplified herein in connection with devices for making x-ray diagnoses such as x-ray tube casings, x-ray image intensifiers and the like which are positioned manually with respect to an examination subject.

It is common practice to support an x-ray tube casing on an overhead suspension that is movable over an x-ray examination table. The casing is usually fastened to an extensible and contractible telescoping assembly which, along with the casing, is suspended from a steel cable. In some prior art arrangements, the casing is raised and lowered with a motor driven cable drum. In other arrangements, the casing is simply counterbalanced or counterpoised so that it will stay at whatever elevation it is set above a patient on an x-ray table.

A known type of manually operable counterpoise system uses a spirally wound flat spring steel strip which is inside of a container. A shaft extends through the center of the spiral for engaging the inner end of the spring. The outer end is fastened to a spirally groove generally axially tapered cam which is journaled on the shaft. The load is suspended on the cable which wraps around the cam and is fastened to the periphery of the cam. Means are provided to preload the spring until its torque just counterbalances the torque produced by the cable acting over the radius of the cam.

One of the problems with this rudimentary spring counterpoised system is that a different spring or a different cam is required for every different load. To meet the requirements of x-ray apparatus precisely, a dozen or more cams may be required. A compromise method for reducing the number of cams is to make one that is suitable for the maximum expected load and then to add lead weights to any lighter load that is to be supported until the total weight equals the maximum in which case fairly satisfactory counterpoising will be obtained. In current practice, a wide variety of x-ray devices having different weights are used in different installations so it is still necessary, using conventional methods, to employ several different cams. However, the cost of the added lead weights, the cost of shipping them and the inconvenience of handling them still remains. Furthermore, any unnecessary weight is manifested as inertia in the system which means that more manual effort must be exerted to position the supported device at the desired elevation.

In some prior art spring counterpoise systems an attempt was made to compensate for using an improper or oversized cam by increasing the preloading of the spring. Winding the spring tighter than it was designed for, however, is at the expense of increasing friction between turns, thus, increasing hysteresis, leading to erratic operation and reduced life.

Another problem in prior counterpoise systems is uneven or eccentric winding of the torsion spring which leads to unduly high friction between turns which may result in overstress and fracture. Eccentric winding is due primarily to the conventional manner of anchoring the spring ends.

Still another problem in prior counterpoise systems resides in the devices which have been used to sense load cable and torsion spring failures. These devices usually depend on an auxiliary cable accepting the load when there is spring or load cable failure, but known devices lock-up when stress is temporarily removed from the load cable, such as due to the x-ray tube casing suddenly decelerating or coming to rest on another piece of equipment, and when this happens prior systems are difficult to reset. Furthermore, in many prior systems the auxiliary or safety cable carries a substantial portion of the load at all times and deteriorates almost as fast as the main load carrying cable.

SUMMARY OF THE INVENTION

An object of the present invention is to provide a spring counterpoise load supporting device which uses a single specially contoured cam capable of supporting a wide variety of individual loads at different times.

Another object is to relate the torque produced by the stress on the load cable acting over the cam radius and the torque produced by the torsion spring in such manner that the probability of the spring becoming overstressed is reduced.

A still further object is to provide a counterpoised system that permits a supported load to be raised and lowered manually in a smooth fashion and without undue effort.

Another object is to provide a method of designing a cam for handling different loads on the same cam at different times.

Still another object is to provide a method for locating a load supporting cable on a cam such that the counterpoise system will handle a particular load.

Another object related to another aspect of the invention is to contain and support the spring in such manner that its spiral turns will maintain better concentricity during winding and unwinding such that frictional losses between turns is reduced.

Another feature of the new counterpoise system is a safety device which can be adjusted for optimum sensitivity to loss of load cable tension for any load value within the expected load range and which locks up when cable tension is reduced but unlocks automatically when normal tension is restored.

In accordance with the invention, corresponding inner ends of one or more spiral springs are fastened to a shaft that is substantially coaxial with the springs. The outer end of the spring is fastened to a cam which is journaled on the fixed shaft. The radii of a continuous spiral groove in the cam vary in a predetermined manner over the axial length of the cam. A variety of different loads or weights can be supported in a counterpoised state from a cable wrapped around the cam. For each different weight, the cable leading from the cam to the supported load makes tangential contact at a point in one of the grooves of the cam which point determines the value of the load that can be counterpoised within the useful range of the torsion spring. Other points of tangency correspond with other loads. The cable extends from the point of tangency and around adjacent grooves towards the largest radius portion of the cam where the cable is attached. A graphical method for determining the contour of the varying radius spiral cam will be disclosed.

The new safety device generally comprises a pivotable mount which carries an idler drum on which the load cable runs. The mount compresses a pair of adjustable coil springs when the load is on the mount. A nontensioned auxiliary safety cable is attached to a separate drum and to the load. The separate drum has a ratchet wheel on it. The mount carries a pawl which is normally clear of the ratchet. If load cable tension is accidentally lost, the compression springs cause the mount to pivot and the pawl to engage the ratchet wheel to thereby transfer the load to the auxiliary cable.

How the foregoing and other more specific features of the invention are achieved, will now be discussed in the ensuing description of a preferred embodiment of the invention in reference to the drawings.

DESCRIPTION OF A PREFERRED EMBODIMENT

Figure 1:
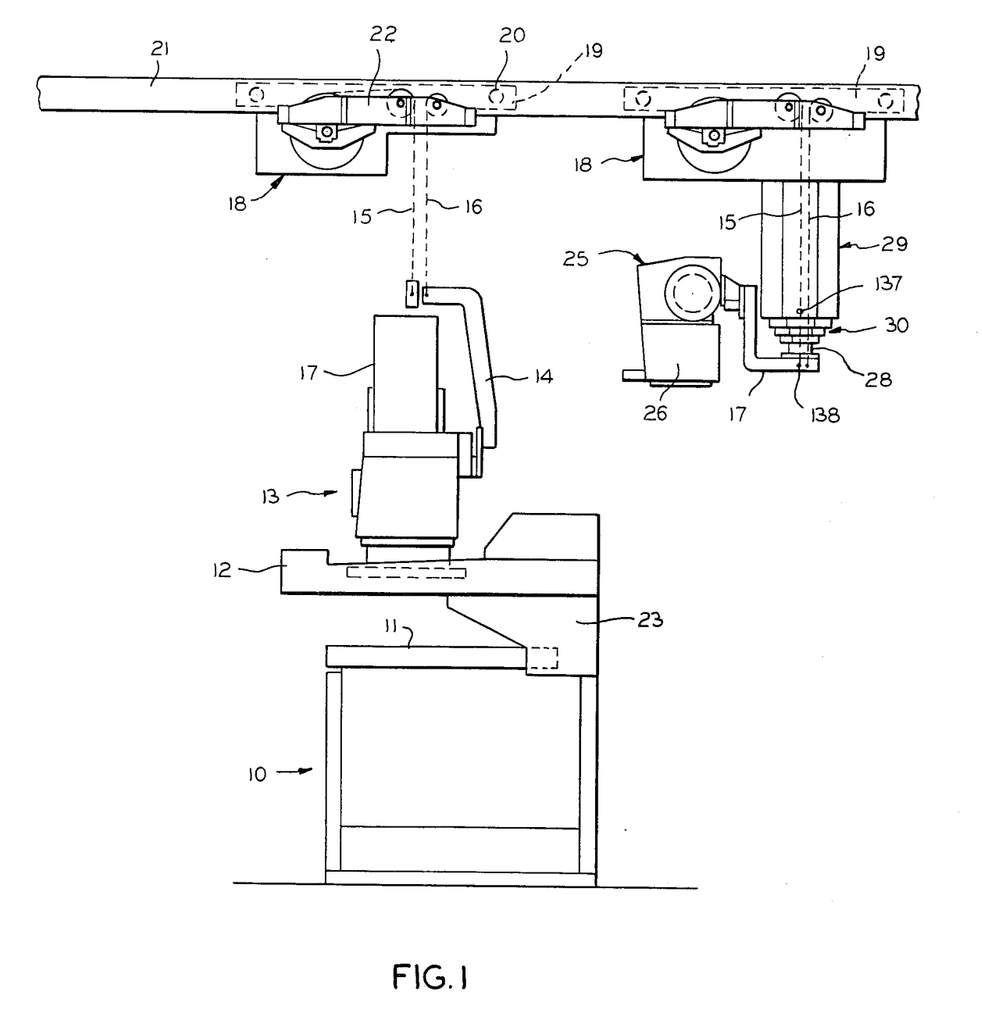
FIG. 1 is an end elevation schematic view of an x-ray table over which an x-ray image intensifier is supported on the new counterpoise support assembly; this view also showing an alternative arrangement wherein an x-ray tube casing is above and over adjacent the table and supported on the new counterpoise assembly.

FIG. 1 shows some typical equipment in a diagnostic x-ray room with which the new counterpoise system may be used. An x-ray table is generally designated by the reference numeral 10. It will be understood that the table may be one that is adapted for longitudinal angulation so that the patient may be positioned vertically, horizontally or in Trendelenburg position while being supported on a table top 11. A spot film device 12 extends laterally over the table top. The spot film device is on a column 23 which is shiftable longitudinally over the table top in a conventional manner. Although it is not shown, there is an x-ray tube within the body of table 10 from which an x-ray beam is projected through the table top and a patient thereon for visualization of an x-ray image with the x-ray image intensifier 13. The intensifier 13 is supported for pivoting about a horizontal axis on an arm 14 by which the whole device is supported from a load cable 15. There is an auxiliary cable, called a safety cable 16, also attached to arm 14 but this cable normally carries no load in accordance with the invention. The image intensifier 13 is engageable with laterally spot film device 12 and can be locked thereto with means which are not shown. The upper housing 17 of image intensifier assembly 13 may contain a variety of components, depending on the users requirements, of different weights and the electronic image intensifier tubes, not shown in detail, may also be of different sizes and weights. For instance, in some applications housing 17 may contain a cine camera and a 105 millimeter photospot camera while another installation may have the photospot camera without the cine camera or with a 35 millimeter camera. The new counterpoise system is provided for supporting a wide variety of loads with the same counterpoise cam and with the same torsion springs and with the same cable. For example, a counterpoise system may be called upon to handle loads ranging from 75 to 300 pounds where the loads comprise radiographic and fluoroscopic equipment.

In FIG. 1, the new counterpoise device is generally designated by the reference number 18 and is seen to be supported near the ceiling of a room on a carriage 19 which has rollers 20 for permitting it to traverse laterally of the room on a beam 21 which may also be movable longitudinally of the room on overhead tracks, not shown. The counterpoise mechanism is mounted on a chassis or casting 22 which is, in turn, fastened to carriage 19.

X-ray tube casings are another type of apparatus which are often supported with a counterpoise system. FIG. 1 shows an x-ray tube casing 25 with a beam collimator 26 attached. The casing is mounted for swiveling on an arm 27 which is fastened to the inner tube 28 of a column 29 comprised of telescoping tube sections such as 30. The counterpoise system 18 may have the characteristics of the one that has just been outlined. It may also be mounted on a carriage 19 which is movable on beam 21. X-ray tube casings, collimators and telescoping columns also come in a variety of sizes and weights which have heretofore required use of a corresponding number of cam and spring assemblied for each load weight or, in the alternative, a lesser number of cams and springs were designed for the maximum weight in a small load range and additional weight was arbitrarily added to the tube casings to establish balance or counterpoising. Weight variations among different models of tube casings and telescoping columns can exceed 40 pounds as is well known. This means that in some installations, 40 or more pounds of weight might have to be added to secure balance or counterpoising. This, of course, increases the mass of the load and requires more effort on the part of the operator to change the elevation of the load. In some prior x-ray tube suspension systems hoists driven with electric motors have been used in conjunction with counterpoising systems to mitigate operational effort due to inertia resulting from unduly high mass.

The general features of the new counterpoise system will now be outlined and this will be followed by a more detailed description of how the new torsion spring and cooperating cam combination is designed to achieve a counterpoise system that is applicable to a range of loads or weights.

Figure 2:
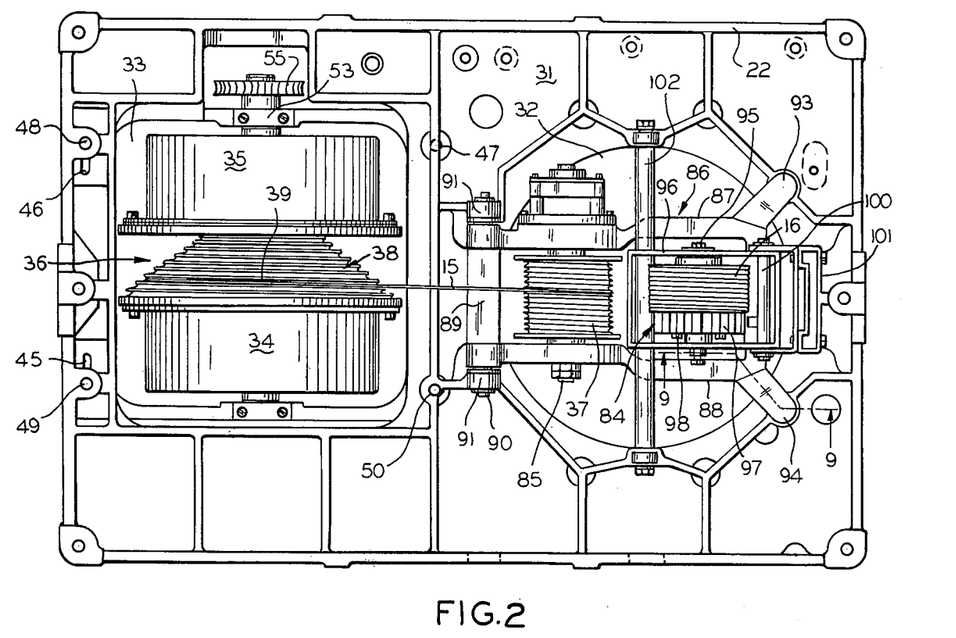
FIG. 2 is a plan view of the counterpoise assembly.
Figure 3:
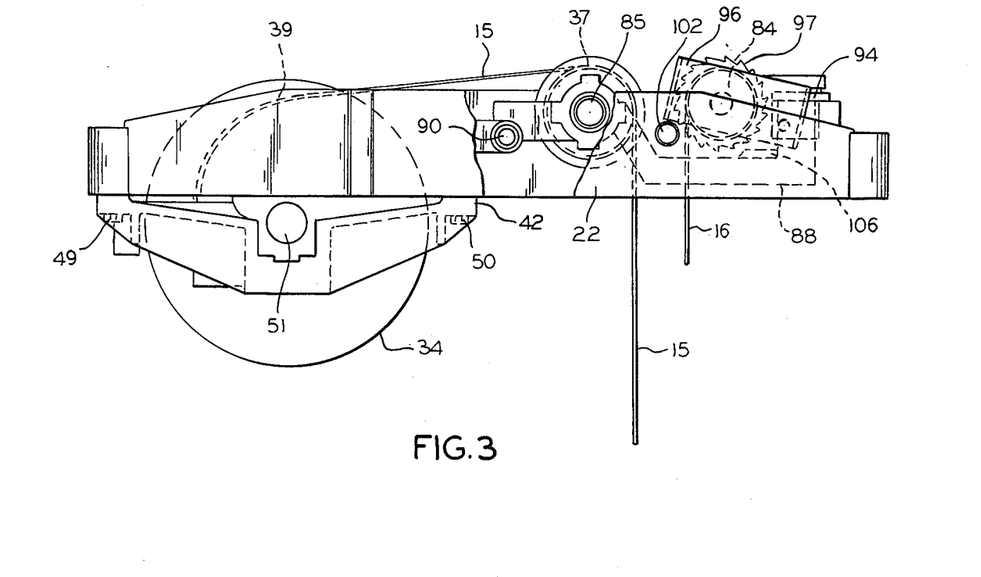
FIG. 3 is a side view of the assembly shown in the preceding figure.

FIGS. 2 and 3 show the chassis or casting 22 of the counterpoise assembly which is mounted to a carriage 19 as was explained in connection with FIG. 1 to permit lateral and longitudinal movement about an x-ray room. The chassis 22 has a bottom 31 in which there are two major openings 32 and 33. Opening 33 is occupied by an assembly comprising a pair of torsion spring housings 34 and 35 between which there is a specially designed cam 36 which will be described in detail later. The cam tapers axially and its periphery is provided with a continuous spiral groove 38 of continuously changing radius, the details of which will be discussed later. The load which is to be supported in a counterpoised state, such as the x-ray apparatus described in connection with FIG. 1, is supported on load cable 15 which runs horizontally in FIG. 2 after it leaves a point of tangency on the cam at approximately where reference numeral 39 is applied. The cable 15 in FIG. 2 runs over a spirally grooved idler drum 37 and then downwardly to the point of attachment on the supported load. The load cable 15 makes at least one full turn around idler drum 37 and is retained in the spiral groove of the idler so that the cable leaves the cam and leads to the drum at minimum angle and misalignment regardless of the extent to which the cable is wound or unwound from the cam.

A description of the counterpoise cam and torsion spring assembly will now be given in reference to FIGS. 2-5. First refer to FIG. 4. The assembly comprises a frame 40 which has flanged ends 41 and 42 in which there are slotted mounting holes 43-46. In FIG. 2 it will be evident that flanges 41 and 42 are secured to the bottom of chassis 22 by means of cap screws 47-50. Slots 43-46 facilitate shifting frame 40 to obtain the best perpendicularity of cable 15 relative to the axes of cam 36 and idler drum 37 regardless of whether the cable is initial taken from the cam on its large or small diameter portions, as hereinafter explained.

Figure 4:
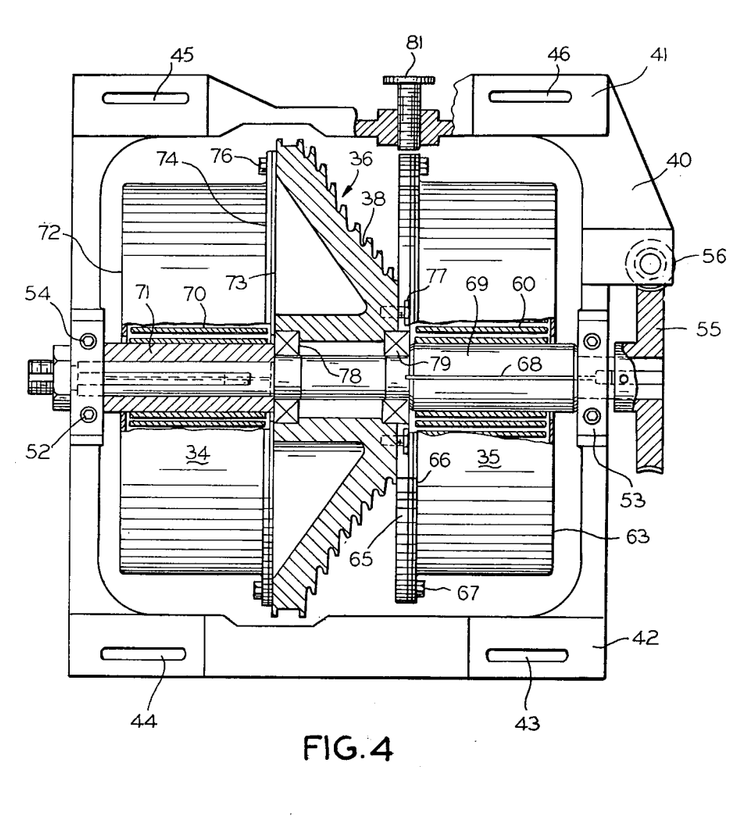
FIG. 4 is a plan view, partially in section, and with parts broken away, of the counterpoise spring, the cam and the supporting frame isolated from the assembly in FIG. 2.
Figure 5:
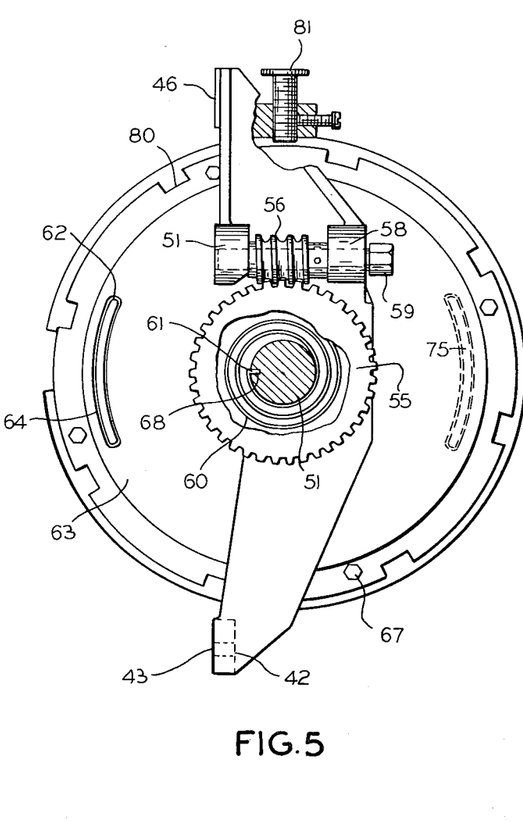
FIG. 5 is a side view of FIG. 4.

In FIG. 4, a shaft 51 is held to frame 40 with bearing clamps 52 and 53. Cap screws such as the one marked 54 secure the clamps. The shaft is turnable in the clamps but the shaft is held stationary by other means during normal operation. A worm gear 55 is fastened to one end of shaft 51. A drive worm 56 meshes with the teeth of gear 55. As can be seen in FIG. 5, worm 56 is journaled for rotation in spaced apart bearings 57 and 58. The worm has a hexagon head 59 which is engageable with a wrench to turn the worm 56 and, hence, gear 55 and shaft 51. The worm gear 55 is only turned when it is desired to preload or remove some or all of the torque exerted on shaft 51 by the counterpoise springs which will soon be described. During normal operation worm gear 55 cooperates with worm 56 to hold shaft 51 against rotation.

Housing 35 is occupied by a torsion spring 60 which is spirally wound from a flat spring steel strip. As shown in FIG. 5, the inner end 61 of spring 60 has a right angular bend which engages in a slot 68 that is in shaft 51. The outer end of torsion spring 60 has a curved anchor member 62 riveted to it and this member enables fastening the outer end of the spring to the spring housing 35. For this purpose, the end wall 63 of spring housing 35 is provided with a complementary curved slot 64 through which one end of curved anchor member 62 extends. A circular plate 65 which is secured to the flange 66 of spring housing 35 with cap screws 67 has a slot similar to 64, not visible, which aligns with curved slot 64 for the other end of curved spring anchor member 62 to extend through. When the spring 60 is installed in housing 35, the spring has a steel band, not shown, around it to prevent its unwinding. The spring is inserted in the housing with plate 65 removed and its inner end 61 slides into slot 68 in the shaft 51. An end of anchor member 62 extends through slot 64. Plate 65 is then installed for its curved slot to receive the other end of the anchor member 62. Since the inner spring end 61 is now connected to the shaft 51 and the outer end is connected to the spring housing with anchor member 62, the torsion spring is subject to being wound and unwound in response to rotation of the spring housing.

Spring housing 34 also contains a torsion spring 70 which is similar to spring 60. Its inner end, not shown, engages with a slot in a sleeve 71 which is keyed to shaft 51. Sleeve 71 is identical in size to an enlarged portion 69 of shaft 51 and is located in the other spring housing 34 and has a slot corresponding with 68 which is diametrically opposite thereto. The end wall 72 of spring housing 34 and its opposed enclosure plate 73 which is held to flange 74 of the housing each have aligned curved slots such as 75 shown in hidden lines in FIG. 5 for receiving the ends of the correspondingly curved spring anchor member such as member marked 62 in FIGS. 10 and 11. The advantage of using curved anchor members 62 which extend a substantial distance circumferentially and support the outer end portions of the flat spring member for some distance will be discussed in more detail later.

Referring again to FIG. 4, it will be seen that spirally grooved counterpoise cam 36 is secured by means of cap screws 76 to spring housing 34 and to its end plate 73. Cam 36 is also secured to the other spring housing 35 by means of cap screws 77, passing through end plate 65 on the housing to the small radius end of cam 36. Shaft 51 has a pair of bearings 78 and 79 such that cam 36 and spring housings 34 and 35 are journaled for joint rotation on shaft 51. When the spring housings and cam are held against rotation, the torsion springs 60 and 70 may be preloaded or given an initial torque by turning worm 56 such that worm gear 55 and shaft 51 are rotated.

Circular plate 65 which encloses an end of spring housing 35 may be provided with a plurality of circumferentially spaced apart slots 80 to enable holding the spring housings and cam against rotation when occasion arises, with a locking screw 81 that is threaded in frame 40.

Figure 10:
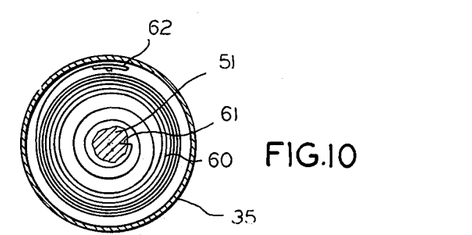
FIG. 10 is a section of the counterpoise spring housing and the torsion spring showing the spring unwound.
Figure 11:
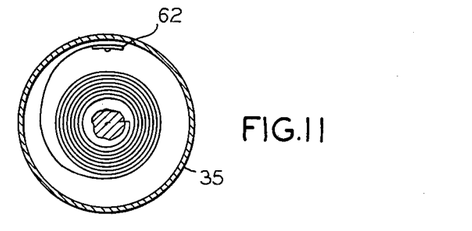
FIG. 11 is similar to FIG. 10 except that the spring is wound.

As implied earlier, use of a curved circumferentially extending anchor member 62 for holding the outer end of the torsion springs 60 is a significant feature. It will be seen in FIG. 10 that the outer end portion of spring 60 overlays curved member 62 to which it is riveted. This provides cantilever support for a portion of the spring which keeps the spring turns concentric when the spring is unwound as in FIG. 10 and tends to maintain the concentricity of the turns when the spring is tightly wound as in FIG. 11. Heretofore, it has been common practice to fasten the outer end of a torsion spring by forming an eye in the end of the spring and fitting the eye over a pin so as to allow the outer end to pivot freely. This prior practice, as is well known, results in the spring turns becoming very eccentric when the spring is wound, that is, tight and bunched up on one side and open and more loose on a diametrically opposite side. This results in high and erratic friction between spring turns as the counterpoised load is raised and lowered so that there are more losses in the system and more effort is required to move the load manually. These disadvantages are overcome to a large extent by the spring anchoring method providing extended support under the spring end portion as illustrated in FIGS. 10 and 11.

Referring to FIG. 2, it will be seen that idler drum 37 over which load cable 15 runs is journaled for rotation on a shaft 85 that is carried on a pivotal mount which is generally designated by the reference numeral 86. Mount 86 comprises a pair of spaced apart arms 87 and 88 which are joined at their pivot end by a cross member 89. Mount 86 is adapted to pivot in a vertical plane on the horizontal axis of a stationary shaft 90 which is carried by support 91 integral with the chassis casting 22. It will be evident in FIGS. 2 and 3 that when there is a load on cable 15, mount 86 will tend to pivot downwardly.

Mount arms 87 and 88 each have extensions 93 and 94. These are to enable the load weight to be supported on springs whose precompressive force is adjustable. The purpose of supporting load mount 86 pivotally and on springs is to obtain cooperation with a safety device which will now be described. The safety device becomes active whenever a counterpoise torsion spring 60 or 70 breaks or loses its torque or when the main load supporting cable 15 breaks. In such case, the load is transferred to and held by the auxiliary safety cable 16.

In FIGS. 2 and 3 it will be evident that safety cable 16 is mounted on a spirally grooved drum 84 which is journaled on a shaft 95. The shaft is fastened in a bracket 96. One end of the safety drum 84 has a ratchet wheel 97 fastened to it coaxially by any suitable means such as screws 98. Normally, safety cable 16 carries no load, it is simply attached to the load and the drum and winds on and unwinds from the safety drum as the load is raised and lowered. A small amount of tension, sufficient to prevent slack from developing in the safety cable 16, is imparted with a helical torsion spring, not shown, which surrounds shaft 95 and is fastened thereto and to the safety cable drum 84.

The safety cable drum 84 support bracket 96 is pivotally mounted on a pin 100 that is carried by a bracket 101 which is secured to chassis 22. It will be evident in FIG. 2 that bracket 96, which carries the safety cable drum, can pivot upwardly toward the observer but not downwardly since bracket 96 normally rests on a tie rod 102. The main mount 86 is normally urged to pivot downwardly by the load weight acting on cable 15. Downward pivoting is normally limited, however, by compression springs 109, to be described, which oppose mount 86.

Figure 9:
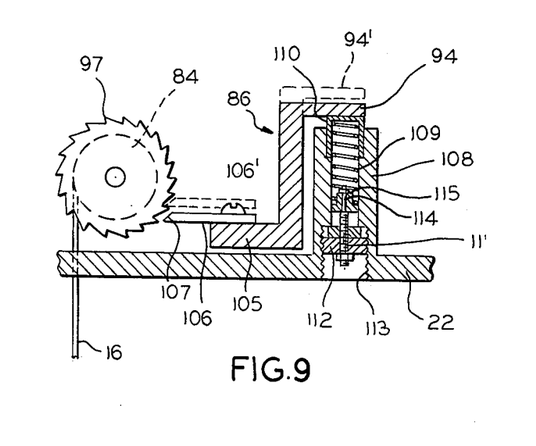
FIG. 9 is a partial vertical section of components of the safety system taken on a line corresponding with 9—9 in FIG. 2.

Refer now to FIG. 9 which shows one of the extensions 94 of mount 86. The extension is normally urged upwardly by spring 109 which is compressed when the mount carries normal load. Adjacent extension 94 on a cross member 105 of mount 86 a pawl 106 is fastened. The beveled tip 107 of the pawl is clear of the teeth on ratchet wheel 97 under normal conditions, that is when there is sufficient tension on the load cable 15. Thus, as explained above, during normal operation the ratchet wheel 97 and the safety cable drum rotate freely as the load is raised and lowered but safety cable 16 has no substantial tension.

If the main load is suddenly removed due to the load supporting cable 15 breaking or due to other reasons such as the load striking another object so as to remove tension from load cable 15 or if torsion spring tension is reduced such as when one torsion spring breaks, mount arm 86 pivots upwardly on shaft 90, counter-clockwise as viewed in FIG. 9, in which case the beveled tip 107 of pawl 106 rises into the path of the teeth of the ratchet. The load to which safety cable 16 is attached is tending to descend and turn the safety drum and ratchet wheel 97 counter-clockwise but such counter-clockwise rotation is limited to substantially little more than the pitch between teeth on the ratchet wheel. The pawl in its actuated state in FIG. 9 is shown in phantom lines marked 106'.

As can be seen in FIG. 9, the extensions such as 94 of the mount 86 are over a tubular element 108 which is integral with chassis 22. The bore of element 108 contains a compression spring 109 which is provided with a bearing cap 110. The precompressive force of spring 109 is set variously in correspondence with the weight of the particular load that is carried by load supporting cable 15. Under normal conditions, when the counterpoise torsion springs 60 and 70 are intact and the load is on cable 15, mount 86 is in its solid line position in FIG. 9 and pawl 106 is disengaged from the ratchet wheel 97 as explained previously. The safety springs 109 can be adjusted for opposing each load weight by turning a screw 11 which threads into a plug 112 which is also externally threaded so it can be retained on the threads 113 of a suitable hole in the chassis 22. A reduced diameter end portion 114 of screw 111 captures a shouldering plug 115 in which reduced portion 114 is rotatable.

An advantage of the safety system discussed in connection with FIG. 9 is that spring 109 can be adjusted to coordinate with any load weight which the counterpoise system is called upon to handle. This means that the sensitivity of the safety system can be properly set. Another advantage is that if the supported load collides with another object such as to remove stress from the load cable, the safety system will set, due to mount 86 pivoting, but as soon as tension is restored to load cable 15, ratchet wheel 97 is automatically released. This contrasts with prior art safety systems wherein when the load cable lost its tension, the safety system locked up and required more extensive measures to release it after the load was restored.

The manner in which the counterpoise cam 36 is designed to accommodate a plurality of different loads instead of a single load or a single load with counterweights added as in the prior art, will now be described. Some specific numerical values for the cam and spring characteristics will be used in the illustrative design procedures to facilitate description but those skilled in the art will be able to convert the information to a more generalized form to design for various counterpoised loads with selected vertical distances.

First of all, a counterpoise torsion spring must be selected which, according to known design techniques, is capable of providing a torque commensurate with the range of loads that are to be supported at different times. Sometimes two counterpoise torsion springs such as 60 and 70 are used since one spring might require an unduly thick and wide flat spring stock or have an inconveniently large diameter when wound.

Figure 12:
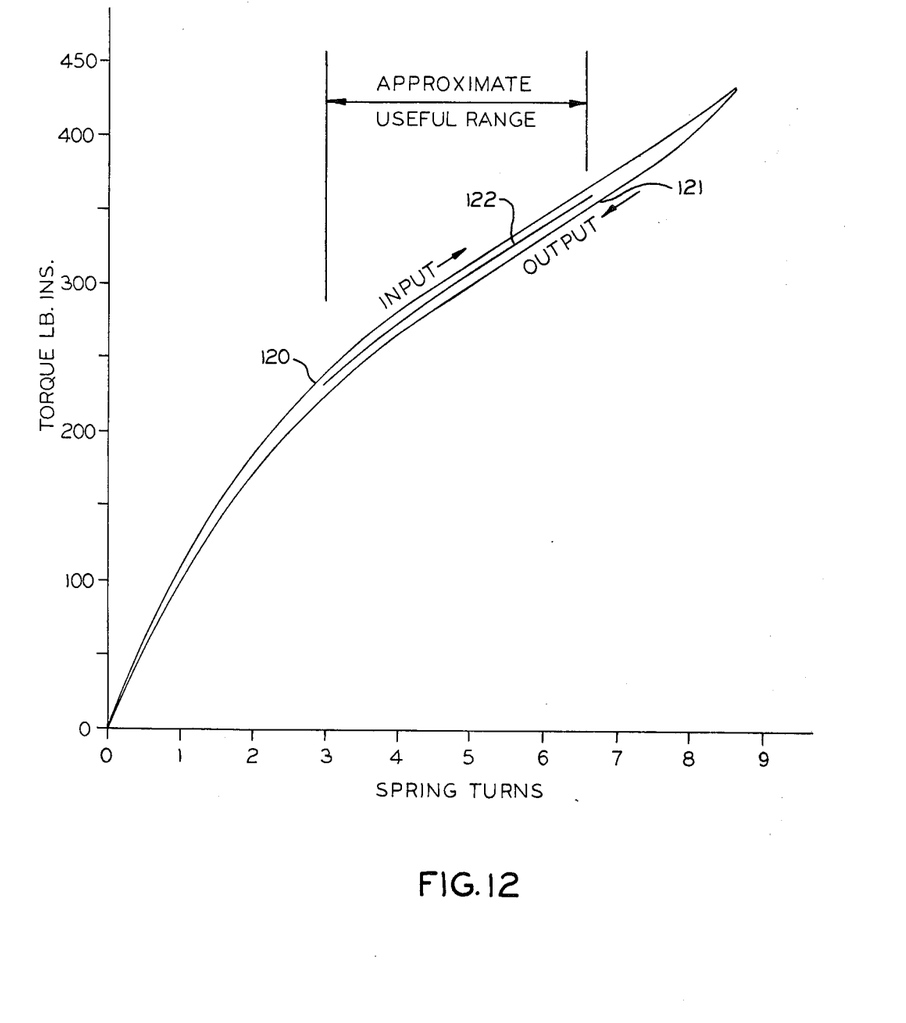
FIG. 12 is a typical graphical plot of torsion spring turns versus torque produced thereby.

Certain characteristics of the counterpoise torsion spring must be considered at the outset of the design. Among these characteristics are the relationship of the spring turns to the torque output of the spring. This is illustrated in FIG. 12. The top line 120 of this plot shows the relationship between the number of spring turns and torque when the spring is in various winding states. The lower line 121 gives the relationship between torque obtainable from the spring and the number of turns. The torque differences between lines 120 and 121 represent hysteresis or loss of power and this is largely due to the fact that energy has to be put into the spring when winding it to overcome friction between turns. The frictional force also acts during unwinding in which case less torque is obtainable for a given number of turns that was put in during winding to the same number of turns. It will be observed in the FIG. 12 example that the relation between spring turns and torque expressed in inch-pounds is quite nonlinear for the first few springs turns about up to the point where the reference number 120 is applied. Likewise, there is poor linearity beyond the number of spring turns where the reference number 121 is applied. An intermediate line 122 which is close to the average torque between the input and output curve is taken as the useful range of the spring. This is roughly between points 120 and 121. The line 122 is not truly linear but it is a good approximation for a useful design range.

In this example, to achieve the maximum longevity of the counterpoise springs consistent with user considerations, the spring will not be wound more than 6.5 turns to keep it in the useable range and assure that it will never be overstressed with expected loads. With some springs, a greater or lesser maximum of turns may be permissible without overstressing. As mentioned in reference to FIG. 12, the design curve 122 then lies between the input and output curve and is equal to or less than 6.5 turns of the spring. The loads to be imposed in this example, on the counterpoise cable 15 are to range between 140 to 220 pounds which are called the load range limits. For the design to be valid, a vertical travel distance of the load between its uppermost and lowermost positions for all loads must be selected. In this example, 60 inches is selected since that is acceptable travel in most instances where x-ray apparatus is suspended on the counterpoise cable as illustrated in FIG. 1. Cable 15 will have a diameter of 0.125 inch since this will carry a load of 220 pounds with a normal margin of safety.

Although the invention contemplates using only one cam for the range of loads as opposed to a cam for each load, the first step is to design a cam for the minimum load to be carried, which in this example, is 140 pounds. Within the useful range of the spring, the torque caused by the weight on the cable acting through a radius moment arm of the cam is equal to the counter torque produced by the torsion spring. When the load is up, the torsion spring has a least number of turns for producing counterpoising and the load cable 15 is in a relatively small radii groove of the cam 36. As the load is lowered, the spring turns increase in number and the cable shifts to the larger radii portion of the cam, thereby providing a larger moment arm to help the spring force, which is also increasing due to increased turns, counterpoise the load.

The first step in designing a cam for the 140 pound load is to use the graph in FIG. 12. The torque at 6.5 spring turns, using design curve 122, is close to 359 pound-inches. This is doubled to 718 pound-inches since two springs are to be used. Dividing 718 pound-inches by the load of 140 pounds yields a cam radius at the neutral axis of the steel cable (0.4 of cable diameter) of 5.129 inches. Moving down the design curve 122 to 5.5 spring turns, the torque times two equals about 654 pound-inches. Again, dividing by the 140 pounds yields a cam radius of 4.671 inches at the neutral axis of the cable. This process is continued until the total length of the cable accommodated by this cam reaches 60 inches. It is assumed that the cam curve between calculation points, that is, 6.5 turns to 5.5 to 4.5 turns, etc., is a straight line. Theoretically this is not true but the deviation between the spring design curve 122 and a straight line between the calculation points is negligible and simplifies manufacture of these cams.

A curve may now be drawn of cam radius plus 0.4 of the cable diameter (which is the neutral axis of the cable) versus spring revolutions for a 140 pound load. This is done on transparent graph paper. The plot for the 140 pound load of cam radius versus spring revolutions is a slightly curved line extending between the points 122 and 123 in FIG. 13.

The previous steps are conventional practice. Part of the present invention consists, however, in using these conventional steps to provide a composite cam which is capable of supporting a wide range of loads when the tangent point of the cam is properly set as hereinafter set forth. In order to provide the composite cam in the present example, the next cam to be designed will accommodate 150 pounds. A 10 pound load increment was chosen as the practical variation although 5 or 20 pounds could have been used. The design curve 122 in FIG. 12 again yields 359 pound-inches and that is doubled and divided by the new load of 150 pounds to yield a cam radius at the neutral axis of the cable of 4.787 inches. Moving down the design curve to 5.5 turns, the double torque of 6.504 pound-inches is again divided by 150 pounds to produce a cam radius at the neutral axis of the cable of 4.360 inches. This process is repeated at 4.5 spring turns, 3.5, etc., until the cable length on the cam is again 60 inches. Another curve can now be drawn of cam radius plus 0.4 of the cable diameter versus spring turns for a 150 pound load. Again, this is done on transparent graph paper. This line has end points 124 and 125 in FIG. 13. The process is repeated for a 160 pound load which results in the line between points 126 and 127 in FIG. 13. The process is continued in 10 pound increments up to the 220 pound load and the graphs are individually plotted on transparent graph paper. In this case there are nine separate graphs on respective transparent sheets.

Figure 13:
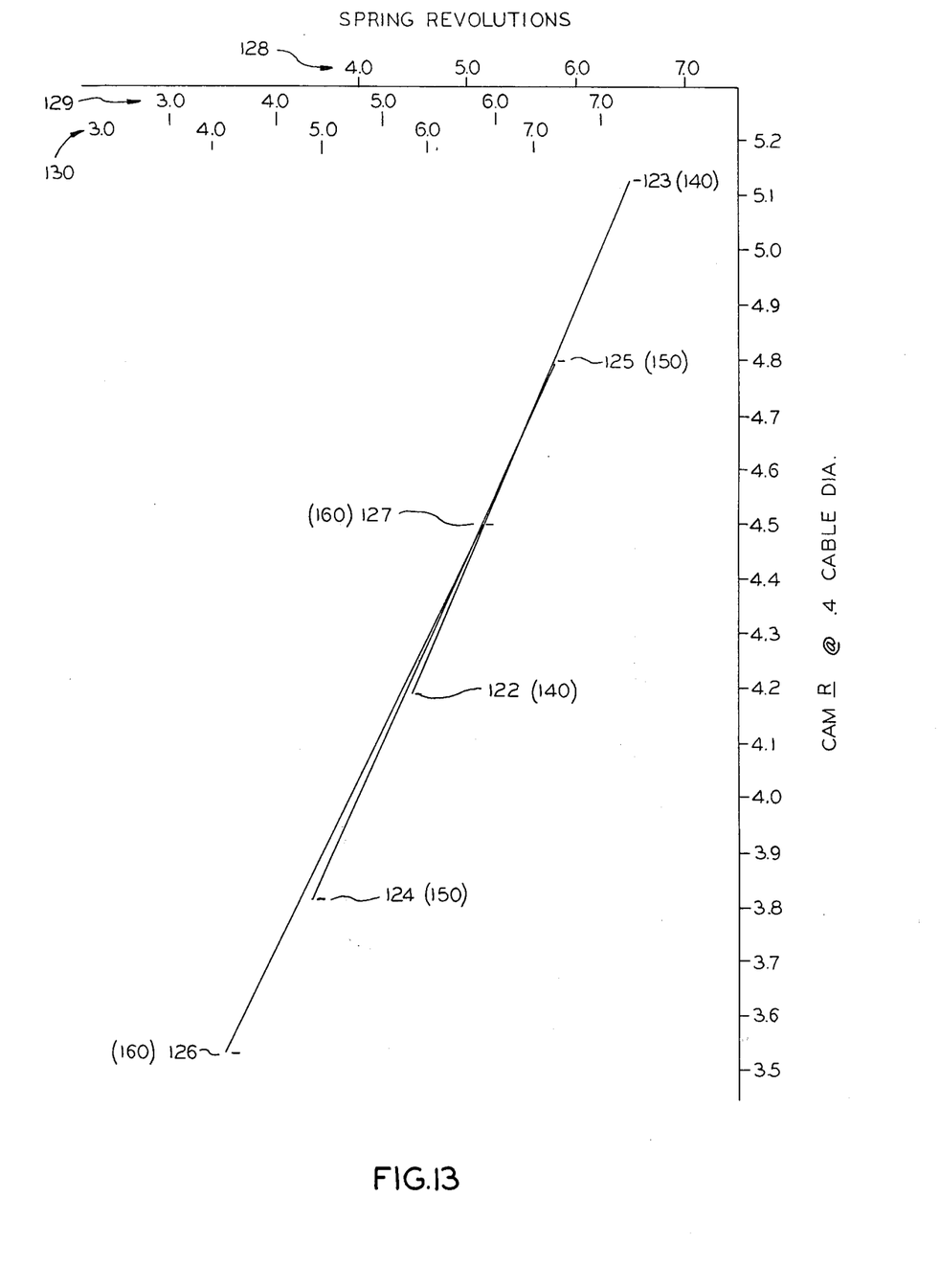
FIG. 13 is a graphical plot of cam radius versus spring revolutions for a few typical load increments.

The individual graphs for the 10 pound load increments are then placed on an illuminated view box with a 140 pound load curve on the bottom. The 150 pound curve is placed over the former and the 160 pound curve over the latter until the 220 pound curve is on top. The ordinate of each of these curves is the cam radius at 0.4 of the cable diameter. When the 150 pound curve is placed on top of the 140 pound curve, the ordinate values, are placed in line or correspondence, that is, the cam radii for the 150 pound curve are placed coincidentally with the same cam radii for the 140 pound curve and the 150 pound curve is moved right or left so that the curves are as coincident as possible. In the FIG. 13 example, the 140 pound curve limited between points 122 and 123 is properly related to the cam radius represented by the ordinates and to spring revolutions represented by the top row 128 of numbers on the abscissa of the graph. In FIG. 13 the load increment is in parenthesis adjacent the reference numerals indicating the cam radius versus spring turns plot terminal points for this load increment. The next curve between the points 124 and 125 for the 150 pound load relates to the second row 129 of spring revolutions. The third curve between points 126 and 127 relates to the third row 130 of spring revolutions. Although only three curves are shown in FIG. 13, it will be understood that all nine curves for each load increment are similarly superposed. The various rows of spring revolutions are positioned as they appear on the individual graphs, but they are seemingly misaligned in FIG. 13 because the first three plots are illustrated as having already been overlaid to align with each other where their cam radii coincide. The curves are valid because for any load within the load range, the cam has a corresponding radius. It should be noted that the individual plots or lines overlap each other to some extent which is indicative of a portion of a cam having a range of radii for one or more loads that overlap and can be used for other loads.

Figure 14:
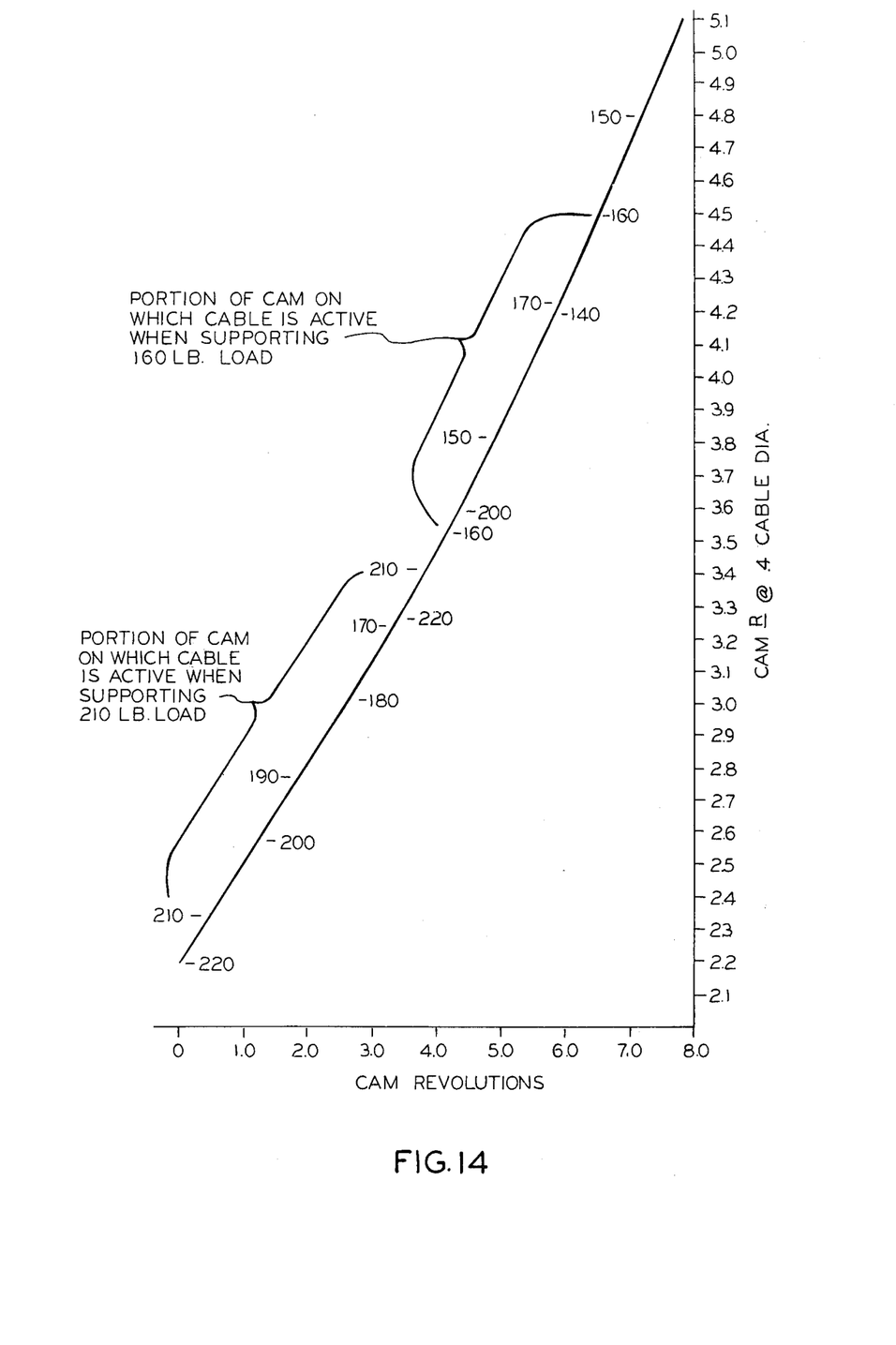
FIG. 14 is a composite graphical plot of cam revolutions versus cam radius for the range of loads that are to be supported with an illustrative counterpoise system.

After the 150 pound curve is placed over the 140 pound curve and moved right or left on equal ordinates until they are as coincident as possible, the two transparent curve sheets are immobilized to prevent shifting. The 160 pound curve is then placed over the 150 pound curve so that their ordinates are equal. This curve is then shifted right or left along the abscissa axis until the curve is aligned as closely as possible with the 150 pound curve beneath it and this sheet is immobilized. The process is continued until all curves for the range of loads between 140 to 220 pounds are superimposed with equal ordinates aligned and immobilized. As is evident in FIG. 13, the individual curves are overlapping and almost coincident although they do separate from each other somewhat. When all of the graphs are superimposed as just discussed, a faired or average curve is drawn through all of the plots and this results in a composite curve which is depicted in FIG. 14. This curve shows the relationship between cam radius and cam revolutions or spring turns for the entire load range. The data taken from FIG. 14 permits a cam to be machined which allows for counterbalancing loads of 140 through 220 pounds by placing the load supporting cable 15 at different points on cam 36 and winding or unwinding the counterpoise springs accordingly. The cam can be machined with a tracer lathe which is well known. It is clear from FIG. 14 that the composite curve is nonlinear. As a result, the cam radius rate of change is continuously variable along the axial extent of the cam. In most prior art designs an attempt was made to work within the linear range and the cam radius changed at nearly a constant rate.

In FIG. 14, portions of the cam on which the cable is active when supporting a particular load, that is, the cam radii range for a particular load traveling a given distance are marked with their load limits. The range for a 210 pound load and a 160 pound are set off with a bracket for illustrative purposes. By way of further example, the smallest radius portion of the cam that is used for the 160 pound load is about 3.53 inches. The largest radius portion required for the 160 pound load is about 4.5 inches. The smallest radius for a given load such as the 3.53 inch radius for the 160 pound load exists at only one point along the constantly changing radius groove of the cam. It is at this point of minimum radius where the cable 16 must make first tangential contact with the cam after which the cable extends around and along 60 inches of cable groove in this case until it passes over the 4.5 inch radius point on the cam which sets off the active length of the cable. Of course, the cable continues over the entire length of the cam from the first point of tangency to the large radius end of the cam where it is fastened to the cam as will be explained. Briefly stated, the cam is characterized by permitting different loads of substantially constant travel distance to be accommodated by merely establishing the cable at a particular first point of tangency with a cam groove as determined by use of the curve in FIG. 14. When this point is determined for a particular load, the counterpoising springs are always operating within their useful range, the manual effort that is required for shifting the load vertically is minimized for any load position, and counterpoising at any point of vertical movement of the load is accomplished.

Figure 6:
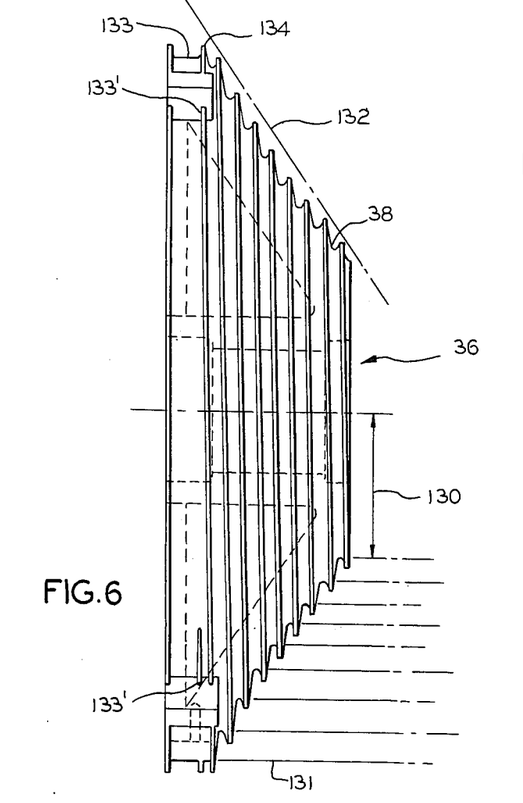
FIG. 6 is an isolated view of the counterpoise cam.

FIG. 6 is an isolated view of cam 36 designed in accordance with the present invention. A light dimension line 130 is applied to indicate the radius of the first turn on the cam which is used for the largest load in the load range. Other light dimension lines 131 are applied to permit visualization of the fact that the cam radius or the radius of the grooves changes continually while advancing from the smallest radius portion of the cable groove to the largest radius portion. A straight dashed line 132 is also applied to permit visualization of the curved contour which the periphery of the cam has as defined by an imaginary line connecting the bottoms of adjacent convolutions of the cable groove.

Figure 8:
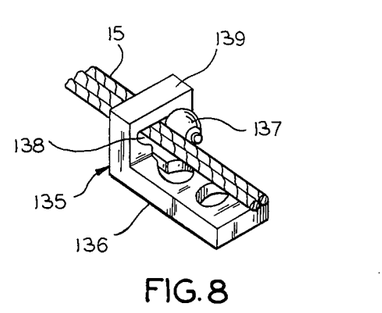
FIG. 8 is a cable anchor with the cable shown fragmentarily.
Figure 15:
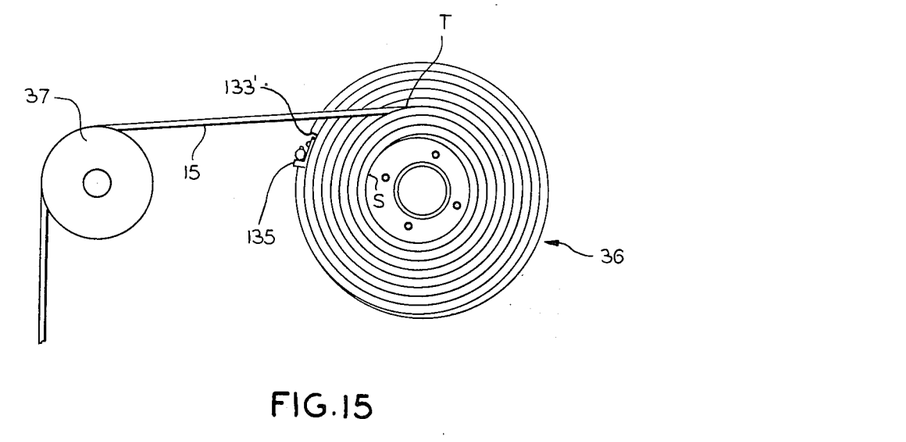
FIGS. 15 and 16 are diagrams for facilitating an explanation of the method whereby the counterpoise system is set up for different loads.
Figure 16:
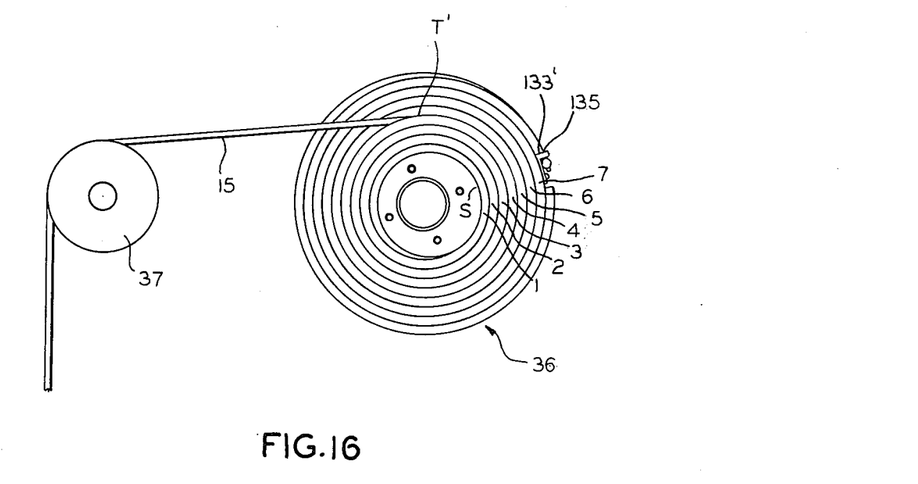

It is desirable to have one cable for all loads in the range. When the cable 15 leading to the load makes a point of tangency with the smallest radius groove of the cam 36, the cable runs over all turns of the grooves and there is no excessive cable. When the point of initial tangency, corresponding with the load being raised to its uppermost position, is within a groove that has a larger radius, there is excess cable and this is accommodated in an annular cable storage channel 133. The inner flange 134 of the channel is provided with circumferentially spaced apart notches 133' through which the cable may enter channel 133 and wrap around it if there is any excess. FIG. 8 shows a cable anchor 135 whose base 136 fits into channel 133 and this anchor can be variously located in channel 133 and screwed down to hold the cable. One of the notches 133' can be considered the first notch when it is desired to count around the periphery of cable storage channel 133 to identify the location of a particular notch. In FIGS. 15 and 16 only the first of a plurality of circumferentially spaced notches 133' is shown and it is on a radial cam line where the tow of groove numbers 1-7 is applied. As will be evident later, the installer's job of establishing the proper initial point of tangency between the load cable and the cam for a particular load weight can be made easier by providing the number of the notch 133' at which cable anchor 135 should be fixed. FIG. 8 also shows the end of the cable 15 with a ball 137 swaged thereon to prevent the cable pulling through a slot 138 in the upstanding leg 139 of anchor 135. Excess turns of cable can be passed through slot 138 as shown.

The manner in which the counterpoise system is used will now be described in reference to FIGS. 7, 8, 15 and 16 primarily. As seen in FIGS. 15 and 16 each turn of the cam groove is assigned a number from one to seven in this case. The starting point of the cam groove is marked S. The first complete and useful turn is marked with the number 1. The installer of the counterpoise system is provided with a chart which tabulates the loads in relation to the point along the cable groove where the leading end of the cable extending from the load makes first tangential contact with the cam groove.

In FIG. 15, for example, the load cable runs over idler drum 37 and makes contact at a first point of tangency marked T. This happens to be for a load of about 203 pounds. Point T is where the cam radius is about 2.57 inches and the supported load is in its uppermost position where the torsion springs have only the initial torque loaded into them with the worm gear and worm. In FIG. 14 one can see that the point of tangency when the load is up so the springs only have preload torque for a 203 pound load corresponds with a cam radius of 2.57 inches. It is easier for the installer to use the turns data to establish the point of tangency T rather than the radius data for a particular load so turns data is provided, otherwise the radius of the point would have to be measured from the cam axis to wherever that particular radius came up along the cam groove. Of course, the cable extends along the groove to the larger diameter portion of the cam and can go to the end thereof. The cable inevitably passes over a second point on the cam groove at which there is about 60 inches of cable within the groove, in this example, going back to the first point of tangency T. The cable is tangent to the cam at or near the second point when the load is at its lowermost position. The fact that the cam is contoured with a continuously varying radius as prescribed earlier assures that the torsion springs will never be loaded beyond their useful design range discussed earlier.

FIG. 16 is included to illustrate a case where the load is about 161 pounds in which case the cable is tangent to the cam at a point marked T' which is at the 3.8 turn when the load is up. Cam radius at the 3.8 turn is about 3.42 inches initially as can be seen in FIG. 14 for this load.

Now to be described is the manner in which the load cable 15 is set on cam 36 so the portion of cable 15 leading from the idler drum 37 and load will make tangential contact at a point in the spiral cable groove where the groove radius is such that the torque caused by the load acting on the cam will be substantially equal and opposite to the torque produced by the torsion springs at the beginning of their useful range corresponding with the load being in its uppermost position.

First of all, with one end of cable 15 attached to the load, the load is supported by any suitable means, not shown, in or slightly above its intended uppermost position. All stored torque in the torsion springs is previously removed by turning worm wheel 55 with worm 56. The point of initial tangential contact between cable 15 and the spiral groove is determined from the curves for the particular load weight that is to be supported. This information can be used to develop a table showing various loads versus end attachment points for the cable 15. This initial tangent point is specified, not in terms of cam radius at the point, but in terms of the number of a notch 133' in the cable storage channel 133 and the number of turns of excess cable to be located within cable storage channel 133. The free end of the cable 15 is wound toward the larger radius end of the spiral groove such that its end reaches the cable storage channel 133 in the cam or makes part of a turn or one or more turns in the cable storage channel, as determined from the above mentioned table, depending on whether the intended final point of tangency is at a small radius point as it would be for a large load weight or at a larger radius point as it would be for a relatively lighter load. Cable end anchor 135 is then clamped in the selected storage notch 133' and there will be slack in the cable at this time.

The slack is then worked back from the large radius part of the spiral groove in cam 36 toward the desired final point of tangency such as T or T' in FIGS. 15 or 16, respectively. The torsion springs 60 and 70 are then given the initial torque corresponding with the beginning of their useful range in their turns versus torque relationship by turning worm 56 so the load on cable 15 will be substantially counterpoised. The temporary support for the load is then removed. If counterpoising is not perfect when the load is uppermost or anywhere in its travel distance, the worm 56 may be turned a minor amount to obtain proper initial torque in the springs for good counterpoising for all vertical positions of the load.

Thus, it is evident that for any load within the design range, it is only necessary to shift the first point of tangency of the cable along the cam groove to secure uniform counterpoising throughout the travel distance of the load and to have enough turns preset in the torsion springs to assure that the useful portion of the spring revolutions versus torque curve is used.

Figure 7:
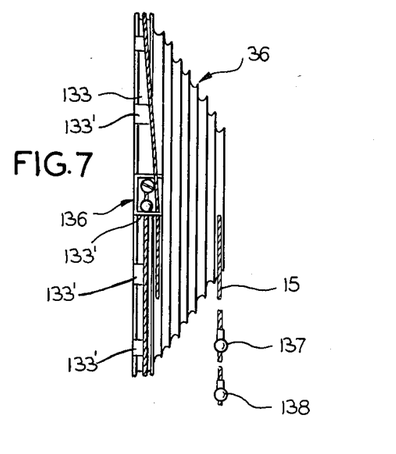
FIG. 7 shows the counterpoise cam and opposite ends of a load supporting cable associated therewith.

FIG. 7 shows the end of the cable 15 with anchor 135 applied. The load supporting end of the cable in FIG. 7 is also shown as having a pair of spaced apart balls 137 and 138 swaged onto it and these balls are similarly marked in FIG. 1 and are for permitting attachment to the object being supported at multiple places so that some of the excess cable beyond ball 137 can simply be coiled up and stored rather than being wrapped around the cam in its storage channel 133.

Although the new counterpoise system and its design have been described in detail, using specific values in some cases to facilitate explanation and understanding, and although the new safety device and outer spring end support have been described in detail, such description is intended to be illustrative rather than limiting, for the principles of the invention can be variously applied and are to be limited only by construing the claims which follow.

I claim:

1. A safety device for use with apparatus including a main cable for supporting a load and means for taking up and feeding out said main cable for raising and lowering said load, said safety device comprising:
   arm means including means for supporting said arm means for pivoting about an axis,
   means on said arm means over which said main cable passes to support said load and impose a force on said arm means which tends to pivot said arm means in a first rotational direction about said axis,
   spring means interposed between said support means and arm means remote from said axis such that said spring means are normally active when there is a predetermined stress in said main cable to urge said arm means to pivot in a direction opposite of that imposed by the main cable,
   auxiliary drum means and means that are independent of said arm means supporting said auxiliary drum means normally for free rotation, said auxiliary drum means being constructed and arranged for winding and unwinding an auxiliary cable therefrom which auxiliary cable is attached at one end to said drum means and at another end to said load, said main cable normally providing substantially all of the support for said load,
   ratchet wheel means having teeth in its periphery and attached to said auxiliary drum means for joint rotation therewith, pawl means mounted on said arm means such as to be clear of said ratchet wheel teeth when said arm means is pivoted in said first direction, loss of said predetermined stress in said main cable causing said arm to pivot in an opposite direction under the influence of said spring means to thereby engage said ratchet wheel to prevent its rotation and transfer said load to said auxiliary cable.

2. A safety device for use with apparatus including a main cable for supporting a load and means for taking up and feeding out said main cable for raising and lowering said load, said safety device comprising:

arm means including means for supporting said arm means for pivoting, spring means interposed between said support means and arm means such that said spring means are normally active when there is a predetermined stress in said main cable to urge said arm means to pivot in a direction opposite of that imposed by the main cable, an idler drum on which said main cable runs to support said load, said idler drum being mounted for rotation on said arm means in spaced relation to the pivot axis of said arm means, said load on said idler drum normally urging said arm means to pivot in a direction opposite to which said arm means is urged to pivot by said spring means, auxiliary drum means and means that are independent of said arm means supporting said auxiliary drum means normally for free rotation, said auxiliary drum means being constructed and arranged for winding and unwinding an auxiliary cable therefrom which auxiliary cable is attached at one end to said drum means and at another end to said load, said main cable normally providing substantially all of the support for said load, ratchet wheel means having teeth in its periphery and attached to said auxiliary drum means for joint rotation therewith, pawl means mounted on said arm means such as to be clear of said ratchet wheel teeth when said arm means is pivoted in said direction, loss of said predetermined stress in said main cable causing said arm to pivot in an opposite direction to thereby engage said ratchet wheel to prevent its rotation and transfer said load to said auxiliary cable.

3. A safety device for use with apparatus including a main cable for supporting a load and means for taking up and feeding out said main cable for raising and lowering said load, said safety device comprising:

arm means including means for supporting said arm means for pivoting, spring means interposed between said support means and arm means such that said spring means are normally active when there is a predetermined stress in said main cable to urge said arm means to pivot in a direction opposite of that imposed by the main cable, said spring arm means comprising compression spring means, means on said support means providing a bore in which said compression spring means is disposed, plunger means in said bore axially of said spring means, adjusting screw means in said bore for advancing and retracting said plunger means to adjust the compression of said spring in correspondence with the selected load weight on said main cable to assure that said pawl will normally be clear of said ratchet, auxiliary drum means and means that are independent of said arm means supporting said auxiliary drum means normally for free rotation, said auxiliary drum means being constructed and arranged for winding and unwinding an auxiliary cable therefrom which auxiliary cable is attached at one end to said drum means and at another end to said load, said main cable normally providing substantially all of the support for said load, ratchet wheel means having teeth in its periphery and attached to said auxiliary drum means for joint rotation therewith, pawl means mounted on said arm means such as to be clear of said ratchet wheel teeth when said arm means is pivoted in said direction, loss of said predetermined stress in said main cable causing said arm to pivot in an opposite direction to thereby engage said ratchet wheel to prevent its rotation and transfer said load to said auxiliary cable.

* * * * *

UNITED STATES PATENT AND TRADEMARK OFFICE
CERTIFICATE OF CORRECTION

PATENT NO. : 4,057,219
DATED : November 8, 1977
INVENTOR(S) : Valentine S. Sobolewski It is certified that error appears in the above-identified patent and that said Letters Patent are hereby corrected as shown below:

Column 16, Line 15 following "spring", delete "arm"

*Signed and Sealed this*

*Twenty-first* Day of *March 1978*

[SEAL]

Attest:

RUTH C. MASON
*Attesting Officer*

LUTRELLE F. PARKER
*Acting Commissioner of Patents and Trademarks*